United States Patent [19]

de Toledo

[11] Patent Number: 4,934,380
[45] Date of Patent: * Jun. 19, 1990

[54] MEDICAL GUIDEWIRE

[75] Inventor: Fernando A. de Toledo, Concord, Mass.

[73] Assignee: Boston Scientific Corporation, Watertown, Mass.

[*] Notice: The portion of the term of this patent subsequent to Nov. 27, 2006 has been disclaimed.

[21] Appl. No.: 275,212

[22] Filed: Nov. 23, 1988

Related U.S. Application Data

[63] Continuation-in-part of Ser. No. 126,042, Nov. 27, 1987, Pat. No. 4,830,023.

[51] Int. Cl.$^5$ .............................................. A61M 25/00
[52] U.S. Cl. .................................... 128/772; 128/657
[58] Field of Search .......................... 128/772, 656–658, 128/341–345; 604/164–170, 280–282, 95; 606/191, 194–195

[56] References Cited

U.S. PATENT DOCUMENTS

| | | |
|---|---|---|
| 2,118,631 | 4/1935 | Wappler . |
| 2,560,915 | 4/1947 | Bamberger . |
| 3,528,406 | 10/1965 | Jeckel .................... 128/772 |
| 3,749,086 | 7/1973 | Kline et al. ................ 128/2m |
| 3,757,768 | 9/1973 | Kline ....................... 128/772 |
| 3,789,841 | 2/1974 | Antoshkiw ............... 128/772 |
| 3,868,956 | 3/1975 | Alfidi et al. ............... 128/345 |
| 3,890,977 | 6/1975 | Wilson ..................... 604/281 |
| 3,906,938 | 9/1975 | Fleischhacker .......... 128/772 |
| 4,003,369 | 1/1977 | Heilman et al. ........ 128/772 X |
| 4,019,925 | 4/1977 | Nenno et al. . |
| 4,020,829 | 5/1977 | Willson et al. ........ 128/772 X |
| 4,534,363 | 8/1985 | Gold ........................ 128/772 |
| 4,538,622 | 9/1985 | Samson et al. .......... 128/772 |
| 4,545,390 | 10/1985 | Leary ...................... 128/772 |
| 4,619,274 | 10/1986 | Morrison ................. 128/772 |
| 4,665,906 | 5/1987 | Jervis . |
| 4,676,249 | 6/1987 | Arenas et al. ........... 128/657 |
| 4,715,378 | 12/1987 | Pope, Jr. et al. ........ 128/344 |
| 4,719,924 | 1/1988 | Crittenden et al. ...... 128/772 |
| 4,721,117 | 1/1988 | Mar et al. ................ 128/772 |
| 4,724,846 | 2/1988 | Evans, III ................ 128/772 |
| 4,748,986 | 6/1988 | Morrison et al. ........ 128/772 |
| 4,779,628 | 10/1988 | Machek ................... 128/772 |
| 4,827,941 | 5/1989 | Taylor et al. .......... 128/772 X |
| 4,830,023 | 5/1989 | De Toldeo et al. .... 128/657 X |

FOREIGN PATENT DOCUMENTS

| | | |
|---|---|---|
| 0141006 | 5/1983 | European Pat. Off. . |
| 0255234 | 2/1988 | European Pat. Off. . |
| 0274130 | 7/1988 | European Pat. Off. . |
| 0274412 | 7/1988 | European Pat. Off. . |
| 0279959 | 8/1988 | European Pat. Off. . |
| WO8800844 | 2/1988 | World Int. Prop. O. . |

OTHER PUBLICATIONS

Cope, "Stiff Fine-Needle Guide Wire for Catherization and Drainage," Radiology, 147: 264 (1983).
ACS, "The Unique Tad Guide Wire," Microglide.

Primary Examiner—Angela D. Sykes
Attorney, Agent, or Firm—Fish & Richardson

[57] ABSTRACT

A medical guidewire has an elongated body that has a degree of flexibility and a distal tip region of relatively greater flexibility. The guidewire consists of a core having a body of first diameter, a distal portion of a relatively smaller diameter, and a generally flat distal end. The end is disposed in the tip region and is spaced proximally from a round tip element that defines the distal end of the guidewire. The distal portion of the core is formed of nitinol. A first coil is joined at its proximal end to the core body by a coupling or crimp ring and extends along the core to a termination point in the distal tip region, proximal of the end portion of the core. A relatively more flexible second coil has a proximal end joined to the first coil and has a distal end joined to the round tip element. A safety wire is secured to the core and has a generally flat distal end within the second coil, joined to the round tip. A transition wire is secured to the core and has a generally flat distal end that terminates within the second coil intermediate of the distal ends of the core and safety wire. The safety wire and transition wires are secured to the coupling.

13 Claims, 3 Drawing Sheets

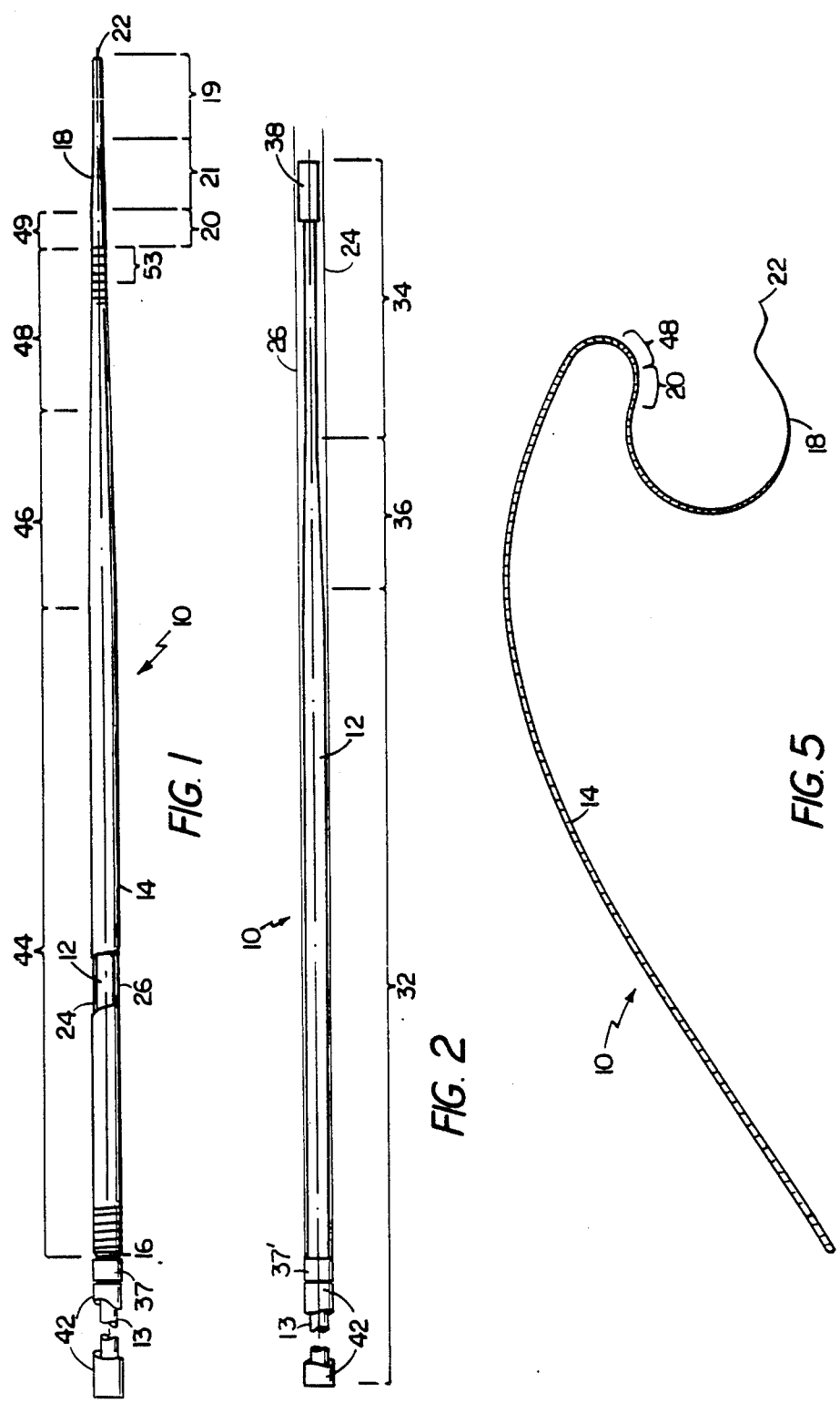

MEDICAL GUIDEWIRE

BACKGROUND OF THE INVENTION

This application is a continuation-in part of U.S. patent application Ser. No. 126,042. filed Nov. 27, 1987, and entitled "Medical Guidewire", now U.S. Pat. No. 4,830,023 issued May 16, 1989, the disclosure of which is incorporated by reference herein.

The invention relates to medical guidewires, e.g., for navigation of narrow passages of a body. A physician introduces the distal end of the guidewire into the body, e.g., via a puncture opening, and, observing the progress of the guidewire via radioscope, attempts to manipulate the flexible tip of the guidewire, e.g., by rotation of the proximal end of the guidewire out side the body, to enter desired passageways and follow their convolutions to a treatment site. A catheter or other medical device may then be advanced over the guidewire to the site.

SUMMARY OF THE INVENTION

According to the invention, a medical guidewire has an elongated body that has a first flexibility and a distal tip region of a second relatively greater flexibility. The guidewire includes core having a body portion of a first diameter, a distal portion terminating in a relatively smaller diameter, and a generally flat or rounded distal end portion. The end portion is disposed in the tip region and spaced proximally from a round tip element that defines the distal end of the guidewire, the distal portion being formed of nitinol. A first coil is joined to the body portion of the core at its proximal end by a crimp ring or coupling and extends along the core to a termination point in the distal tip region, proximal of the end portion of the core. A relatively more flexible second coil has a proximal end joined to the first coil and a distal end joined to the round tip element. A safety wire is secured to the core, the safety wire having a generally flat distal end portion within the second coil, joined to the round tip element, a transition wire is also secured to the core, the transition wire having a generally flat distal end portion disposed to terminate within the second coil intermediate of the distal end portions of the core and of the safety wire. The safety wire and transition wire are secured to the coupling or crimp ring.

Preferred embodiments of this aspect of the invention have one or more of the following features. The generally flat distal end portions of the core, safety wire and transition wire are of predetermined axial extent, and the generally flat distal end portion of the transition wire is disposed to span a gap between the proximal end of the safety wire end portion and the distal end of the core end portion. At least one of the safety wire and the transition wire is a flat ribbon wire. At least one of the safety wire, the transition wire, the second coil and the round tip element are of radiopaque material, e.g., comprising platinum. The first coil in a first region preceding the second coil has a first outer diameter and in a second region distal to the first region the first coil has a second, relatively smaller outer diameter, and the second coil, in a proximal region adjacent the first coil, has an outer diameter substantially equal to the first outer diameter of the first coil and an inner diameter substantially equal to the second outer diameter of the first coil, and the proximal region of the second coil is disposed about the second, smaller diameter region of the first coil. Preferably the diameter of the first coil in the first region is substantially uniform, and the diameter of the first coil in the second region is substantially uniform, and the first region lies immediately adjacent the second region. Also, the relatively smaller second diameter of the second region of the first coil is formed by removal of coil wire material from the exterior of the coil, preferably by grinding. The first coil and the second coil are joined in the proximal region of the second coil. Adjacent windings of the first coil in the region proximal of joining to the second coil are relatively more spaced than adjacent windings of other, more proximal regions of the first coil The first coil terminates distal of the proximal end of the core and the guidewire further comprises a sleeve of polymeric material, preferably polytetrafluorethylene (PTFE) or polyethylene, disposed about the core. The sleeve terminates distally adjacent to a crimp ring or coupling or the proximal end of the first coil and the outer diameter of the first coil near the sleeve termination point is equal to or greater than the outer diameter of the adjacent sleeve.

In a second aspect, the invention features a medical guidewire comprising a core and a coil wire, the core having a proximal portion formed of stainless steel, and a distal portion formed of nitinol, the coil wire extending over a minor portion of the length of the guidewire. Preferably the coil wire has a distal portion formed of platinum; and the distal portion of the core is joined to the platinum in the distal portion of the coil wire.

In a third aspect, the invention features a medical guidewire having an elongated body that has a first flexibility and a distal tip region of a second relatively greater flexibility. The guidewire includes a core having a body portion, and an end portion disposed in a tip region and spaced proximally from a round tip element that defines a distal end of the guidewire. A coil is joined to the body portion of the core at its proximal end and extends along the core to a termination point at the distal tip. A safety wire is secured to the distal tip, and a sleeve is positioned around the core and extending to a region near the distal tip. The sleeve is secured to the safety wire, and transmits torque to the distal tip.

Attributes sought by physicians employing guidewires include high torque response of the distal tip within the body to rotation of the portion outside the body; stiffness over much of the length for transmission of axial pressure; a flexible tip to facilitate manipulation into side branches and through convoluted passages and also to avoid patient trauma; and also a radiopaque tip region for clear viewing. The guidewire of the invention features these attributes and further provides a relatively smooth transition from the relative stiff proximal portion of the guidewire to the flexible distal tip. The use of nitinol in the tip region increases its flexibility.

These and other features and advantages of the invention will be apparent from the following description of a presently preferred embodiment, and from the claims.

DESCRIPTION OF THE PREFERRED EMBODIMENTS

We first briefly describe the drawings.

Drawings

FIG. 1 is a side view partially in section of a medical guidewire of the invention;

FIG. 2 is a top plan view of the core, safety and transition wires and sleeve of the guidewire of FIG. 1;

FIG. 5 is a somewhat diagrammatic representation of the guidewire flexed to show the smooth transition of flexibility.

STRUCTURE

Figure 4:
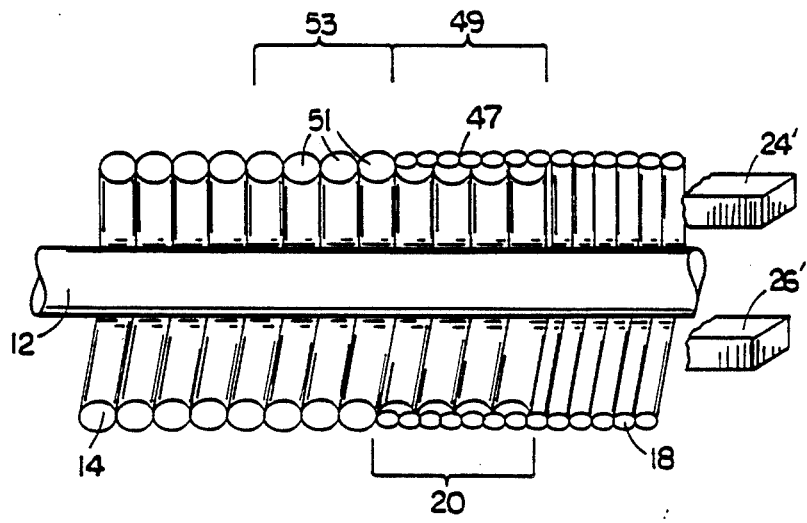
FIG. 4 is a side section view of the coil-to-coil joint.

Referring to FIGS. 1 and 2, a guidewire 10 of the invention has an elongated proximal core element 13 and distal core element 12 joined by a coupling 37, a first coil 14 joined at its proximal end 16 to coupling 37, and a second coil 18 joined to the distal end of the first coil at 20 and extending distally to a distal round end trip element 22, e.g., a weldment.

Figure 3:
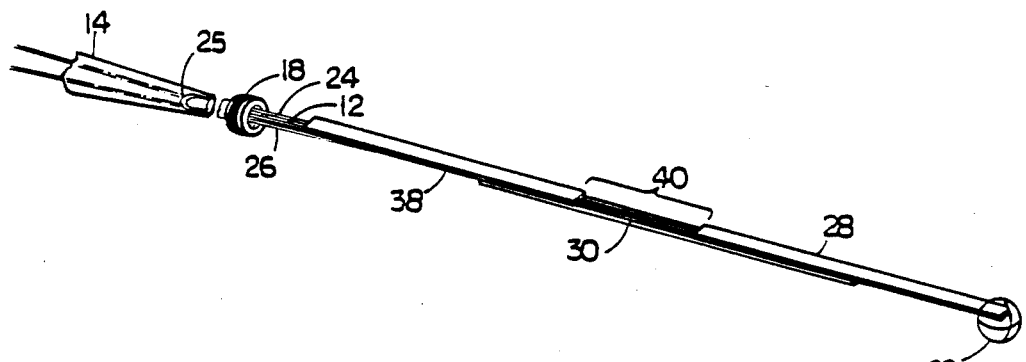
FIG. 3 is a perspective view partially in section of the distal tip region of the guidewire of FIG. 1.

Referring to FIG. 3, disposed within the distal portion of first coil 14 and extending along within second coil 18, along the distal portion of core 12, are safety wire 24 and transition wire 26, e.g., platinum or stainless steel wire, having a diameter of 0.003 inch., or a cross section of 0.002 inch by 0.005 inch. Safety and transition wires 24, 26 terminate distally in generally flat end portions 28, 30 respectively, e.g., about 10 mm long by 0.005 inch wide by 0.0012 inch thick, obtained in this size or formed by flattening the ends of the wires. The distal end of safety wire 24 extends and is joined, e.g., by soldering (or brazing, spot welding, bonding or T.I.G. (tungsten inert gas) welding) to form a distal round end tip element 22. Transition wire 26 terminates distally within second coil 18, spaced about 7 mm from tip element 22. Transition wire 26 and safety wire 24 are typically formed of two wires, attached to core element 12 at their proximal ends by coupling 37 (FIG. 1) or crimp ring 37' (FIG. 2).

Distal core element 12, e.g., about 40 cms long, has a body portion 32, e.g., 0.020 inch diameter, and a tip portion 34, e.g., 0.003 inch diameter and 8.0 cm long, with a smoothly tapering portion 36, e.g., about 5.5 cm long, all formed of nitinol (e.g., as described in Sakamoto et al., E.P.A. 0,141,006, the disclosure of which is incorporated herein by reference) therebetween. Proximal core element 13 is formed of stainless steel or nitinol. If formed of nitinol, coupling 37 may be replaced by a crimp ring, with the proximal and distal core elements being integral. Body 32 of the core forms generally the body of the tip section of the guidewire, while the tapering and tip portions 36, 34, in combination with the other components described, define a distal tip region of relatively greater flexibility, the guidewire smoothly becoming more flexible in the direction of the tip. Tip portion 34 of core 12 terminates distally in a flat distal end 38, e.g. about 10 mm long by 0.005 inch wide by 0.0012 inch thick, formed by flattening the end of the core wire. Core 12 extends distally within the second coil and terminates (FIG. 3 at a position spaced, e.g., about 10 mm from tip element 22.

As shown, the core wire is positioned to leave a gap 40 between end portions 28, 38 of safety wire 24 and core 12, and an end portion 30 of the transition wire is disposed to bridge the gap. The result is a smooth transition of flexibility to the tip, as described more fully below with reference to FIG. 5.

Disposed about the proximal portion of the body of the core is a sleeve 42, e.g., polytetrafluorethylene (PTFE) heat shrunk tightly about the core 12, or polyethylene. Typically, prior to heat shrinking, the sleeve has a 0.060 inch outer diameter and 0.003 inch wall. The sleeve is disposed in position about the core and heated to 800° F., e.g., with a hot air blower or in an oven or by other suitable means, to shrink the sleeve to engage tightly about the core.

First coil 14, e.g., made from stainless steel wire having a diameter of 0.007 inch formed into a pre tension coil, has a proximal portion 44 with an outer diameter of about 0.035 inch and tapers in the region 46, corresponding generally to the tapering portion 36 of the core 12, to a distal portion 48 having an outer diameter of 0.025 inch. Coil 14 is joined to coupling 37 at 16, adjacent the distal end of sleeve 42. (The outer diameter of the sleeve is equal to or preferably less than the outer diameter of the coil as shown.)

Second coil 18 is formed of a radiopaque material, e.g., platinum, for enhanced visibility within the body via radioscope. Coil 18 is a 0.003 inch diameter wire formed into a coil having an outer diameter at its proximal end (region 20) corresponding to the outer diameter of the adjacent end of first coil 14, e.g., 0.025 inch, and a consequent inner diameter of 0.019 inch. The second coil tapers (region 21) to a flexible proximal portion 19 about 30 mm long with an outer diameter of about 0.018 inch.

Referring to FIG. 4, first coil 14 and second coil 18 are joined by removing wire material from the outer diameter of the first coil, e.g., by grinding, to a depth substantially equal to the diameter or thickness of the wire forming the second coil. Preferably, the wires of the first and second coils are sized so no more than one half of the diameter of the first coil must be removed. As a result, removal of material from the exterior of the first coil provides a smooth flat surface for joining of the second coil and the windings of the first coil remain engaged under pretension. (Removal of more than one half of the diameter will result in a soft, loose coil). The proximal end of the second coil is disposed over the distal end 49 of first coil 14 in region 20 and the two are joined, e.g., by solder 47 or the like. To further enhance the smoothness of the transition from relatively stiff first coil 14 to more flexible second coil 18, adjacent windings 51 of the first coil (region 53), proximal of the joint (region 20), are tweaked, i.e., spaced apart, to relieve the pretension set in forming and the windings are permanently deformed in the spaced condition, rendering the first coil relatively more flexible in the region approaching the joint and the considerably more flexible second coil.

The combination of structural features described above, including, without limitation, the materials and the relationships of dimension and construction, results in a guidewire that provides a high degree of torque, i.e., approaching 1-to-1, between rotation of the proximal end and response of the distal tip, and further results in a guidewire having relatively smooth and gradual transition from the guidewire body to the relatively more flexible distal tip. Referring to FIG. 5, guidewire 10 of the invention increases in flexibility in the distal tip region toward the tip.

Figure 6:
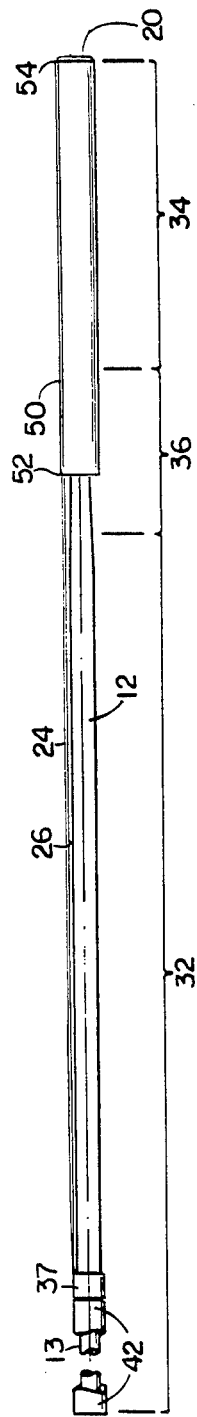
FIG. 6 is a top plan view of an alternative embodiment of a core for a guidewire of the invention.

Other embodiments are within the following claims. For example, referring to FIG. 6, a polyimide torque sleeve 50 is provided jammed at proximal end 52 to core 12 and then attached to core 12 by cyanoacrylate adhesive. Distal end 54 is attached by adhesive to core 12. Safety wire 24 and transition wire 26 are fixed to sleeve 50 by this adhesive and thus whip is reduced at the tip of the guidewire. These wires may terminate at the proximal end of the torque sleeve 50. Sleeve 50 terminates proximally of the distal end of the guidewire so as not to interfere with welding of the tip.

What is claimed is:

1. A medical guidewire having an elongated body that has a first flexibility and a distal tip region of a second, relatively greater flexibility, said guidewire comprising a core having a body portion of a first diameter, a distal portion terminating in a relatively smaller diameter, and a distal end portion, said distal end portion disposed in a distal tip region and spaced proximally from a round tip element that defines a distal end of said guidewire, said distal portion being formed of nitinol, a first coil joined to the body portion of said core at its proximal end at coupling means and extending along said core to a termination point in said distal tip region, proximal of the end portion of the core, a relatively more flexible second coil has a proximal end joined to said first coil and has a distal end joined to the round tip element, a safety wire secured to said core, said safety wire having a generally flat distal end portion within said second coil, joined to said round tip element, a transition wire secured to said core, said transition wire having a generally flat distal end portion disposed to terminate within said second coil intermediate of the distal end portions of said core and of said safety wire, said safety wire and said transition wire being secured to said coupling means.

2. The medical guidewire of claim 1 wherein the generally flat distal end portions of the core, safety wire and, transition wire are of predetermined axial extent, and the generally flat distal end portion of said transition wire is disposed to span a gap between a proximal end of the safety wire generally flat distal end portion and a distal end of a core generally flat distal end portion.

3. The medical guidewire of claim 1 wherein at least one of said safety wire and said transition wire is a flat ribbon wire.

4. The medical guidewire of claim 1 wherein at least one of said safety wire, said transition wire, said second coil and said round tip element are of radiopaque material.

5. The medical guidewire of claim 1 wherein said radiopaque material comprises platinum.

6. The medical guidewire of claim 1 wherein said first coil in a first region preceding said second coil has a first outer diameter and in a second region distal said first region said first coil has a second, relatively smaller outer diameter, and said second coil, in a proximal region adjacent said first coil, has an outer diameter substantially equal to the first outer diameter of said first coil and an inner diameter substantially equal to the second outer diameter of said first coil, and the proximal region of said second coil is disposed about the second, smaller diameter region of said first coil.

7. The medical guidewire of claim 6 wherein the diameter of said first coil in said first region is substantially uniform, and the diameter of said first coil in said second region is substantially uniform, and said first region lies immediately adjacent said second region.

8. The medical guidewire of claim 6 wherein the relatively smaller second diameter of the second region of said first coil is formed by removal of coil wire material from the exterior of said coil.

9. The medical guidewire of claim 6 wherein said first coil and said second coil are joined in the proximal region of said second coil.

10. The medical guidewire of claim 1 or 6 wherein adjacent windings of said first coil in the region proximal of joining to said second coil are relatively more spaced than adjacent windings of other, more proximal regions of said first coil.

11. The medical guidewire of claim 1 wherein said first coil terminates distal of a proximal end of said core and said guidewire further comprises a sleeve of polymeric material disposed about said core.

12. The medical guidewire of claim 11 wherein the material of said sleeve s polytetrafluorethylene (PTFE) or polyethylene.

13. The medical guidewire of claim 11 wherein the sleeve terminates distally adjacent to coupling means or a proximal end of said first coil and the outer diameter of said first coil near the sleeve termination point is equal to or greater than the outer diameter of the adjacent sleeve.

* * * * *